United States Patent
Alhumaid

(10) Patent No.: US 9,517,102 B2
(45) Date of Patent: Dec. 13, 2016

(54) CAUTERY NEEDLE FOR SEPARATING AND/OR PENETRATING THE PERICARDIUM

(71) Applicant: Fawaz Alhumaid, Lake Oswego, OR (US)

(72) Inventor: Fawaz Alhumaid, Lake Oswego, OR (US)

( * ) Notice: Subject to any disclaimer, the term of this patent is extended or adjusted under 35 U.S.C. 154(b) by 290 days.

(21) Appl. No.: 14/224,245

(22) Filed: Mar. 25, 2014

(65) Prior Publication Data

US 2015/0272661 A1 Oct. 1, 2015

(51) Int. Cl.
| | | |
|---|---|---|
| *A61B 17/00* | (2006.01) | |
| *A61B 18/14* | (2006.01) | |
| *A61B 5/0456* | (2006.01) | |
| *A61B 17/34* | (2006.01) | |
| *A61B 18/00* | (2006.01) | |
| *A61B 5/00* | (2006.01) | |
| *A61B 18/22* | (2006.01) | |
| *A61B 18/20* | (2006.01) | |

(52) U.S. Cl.
CPC ......... *A61B 18/1477* (2013.01); *A61B 5/0456* (2013.01); *A61B 5/4836* (2013.01); *A61B 5/7285* (2013.01); *A61B 17/3478* (2013.01); *A61B 18/22* (2013.01); *A61B 2017/00247* (2013.01); *A61B 2017/00703* (2013.01); *A61B 2018/00595* (2013.01); *A61B 2018/00601* (2013.01); *A61B 2018/00702* (2013.01); *A61B 2018/00839* (2013.01); *A61B 2018/2005* (2013.01)

(58) Field of Classification Search
CPC . A61B 5/0456; A61B 5/4836; A61B 18/1477; A61B 5/7285; A61B 17/3478; A61B 18/22; A61B 2017/00247; A61B 2017/00703; A61B 2018/00595; A61B 2018/00601; A61B 2018/00702; A61B 2018/00839; A61B 2018/2005; A61B 18/14; A61B 17/34; A61B 18/24
USPC . 600/508, 509, 185, 431; 606/185; 604/500, 604/506, 507, 272

See application file for complete search history.

(56) References Cited

U.S. PATENT DOCUMENTS

| | | | |
|---|---|---|---|
| 2007/0161916 A1* | 7/2007 | Zantos | A61B 5/0456 600/517 |
| 2008/0208184 A1* | 8/2008 | Davies | A61B 18/1492 606/34 |

(Continued)

FOREIGN PATENT DOCUMENTS

WO WO 2012/048242 A1 4/2012

*Primary Examiner* — Eric Rosen
*Assistant Examiner* — George J Ulsh
(74) *Attorney, Agent, or Firm* — Oblon, McClelland, Maier & Neustadt, L.L.P.

(57) ABSTRACT

A pericardial needle that punctures a pericardial membrane with cautery to attain access into a pericardial space of a heart by positioning a cautery needle tip adjacent to or in contact with a parietal pericardium of the heart such that the puncturing does not damage the heart muscle. The pericardial needle punctures the parietal pericardium when the heart muscle moves towards the pericardial needle, away from the pericardial needle, is at rest and/or is in synchronization with the systolic contraction period of the cardiac cycle of the heart. The synchronization may be provided based on a surface electrocardiogram, an arterial pressure, or a sensing pressure at the tip of the pericardial needle when the pericardial needle is adjacent into the parietal pericardium of the heart.

20 Claims, 13 Drawing Sheets

(56) References Cited

U.S. PATENT DOCUMENTS

2008/0294251 A1 11/2008 Annest et al.
2010/0274129 A1 10/2010 Hooven
2010/0331854 A1 12/2010 Greenberg et al.
2012/0095434 A1 4/2012 Fung et al.
2012/0316611 A1* 12/2012 Armoundas ....... A61B 5/02405
   607/7

* cited by examiner

CAUTERY NEEDLE FOR SEPARATING AND/OR PENETRATING THE PERICARDIUM

CROSS REFERENCE TO RELATED APPLICATIONS

The present application also contains subject matter related to that described in co-pending U.S. patent application Ser. Nos. 13/625,498 and 13/943,542, the contents of which are incorporated herein by reference in their entirety.

GRANT OF NON-EXCLUSIVE RIGHT

This application was prepared with financial support from the Saudi Arabian Cultural Mission (SACM), and in consideration therefore the present inventor has granted The Kingdom of Saudi Arabia a non-exclusive right to practice the present disclosure.

BACKGROUND

Field of the Disclosure

The present disclosure relates to a pericardial needle that punctures the pericardial membrane, preferably with cautery. More specifically, the present disclosure relates to a pericardial needle that punctures the pericardial membrane by synchronizing energy delivery with cardiac muscle motion.

SUMMARY

The present disclosure relates to a pericardial needle that includes a cautery needle for cutting and/or penetrating the pericardial membrane. In one embodiment the disclosure relates to a pericardial needle that includes a lumen, a side arm, and a valve. The pericardial needle also includes a handle connected to the needle. The tip of the cautery needle is located at a puncture end of the pericardial needle. The needle is connected to an external cautery source. Upon instruction the cautery needle may be activated to deliver a pulse of cautery (cut) energy at a penetration or cutting point such as a pericardial membrane. The cautery/energy pulse can be delivered during various phases of the cardiac cycle.

BRIEF DESCRIPTION OF THE DRAWINGS

A more complete appreciation of the present application and many of the advantages thereof will be readily obtained as the same becomes better understood by reference to the following detailed description when considered in connection with the accompanying drawings, wherein.

DETAILED DESCRIPTION

As cardiac medical care advances, there are increasing number of therapeutic procedures that require access into the pericardial space. Examples of such procedures include but are not limited to those needed for pacemakers, defibrillators, and ablation of certain arrhythmias. The pericardial space is a virtual space between the outside of the heart muscle and a thin layer of tissue that encases the heart muscle, called the parietal pericardium. The pericardial space contains a small amount of fluid, called the pericardial fluid.

The pericardial fluid is in constant contact with the heart muscle and the coronary arteries, and therefore, may be used, for example, to deliver drugs to the heart muscle and/or the coronary arteries. Since the pericardial fluid is of relatively low volume, such a method for drug delivery requires a relatively lower dose of drug.

Additionally, the pericardial fluid may be used to introduce an agent into the pericardial space, while localizing the agent to the area around the heart muscle. Such agent is contained within the pericardial fluid, without contaminating other tissue or parts. Also, due to the low turn over rate of the pericardial fluid, such agent is sustained over a relatively long period of time.

Figure 1A:
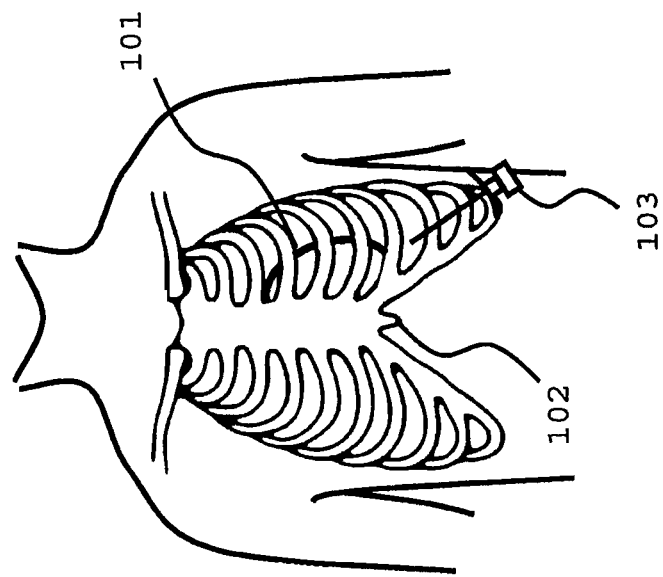
FIGS. 1A and 1B are exemplary illustrations of two exemplary locations on the chest that may be used for the insertion of a pericardial needle to access the pericardial space of the heart.
Figure 1B:
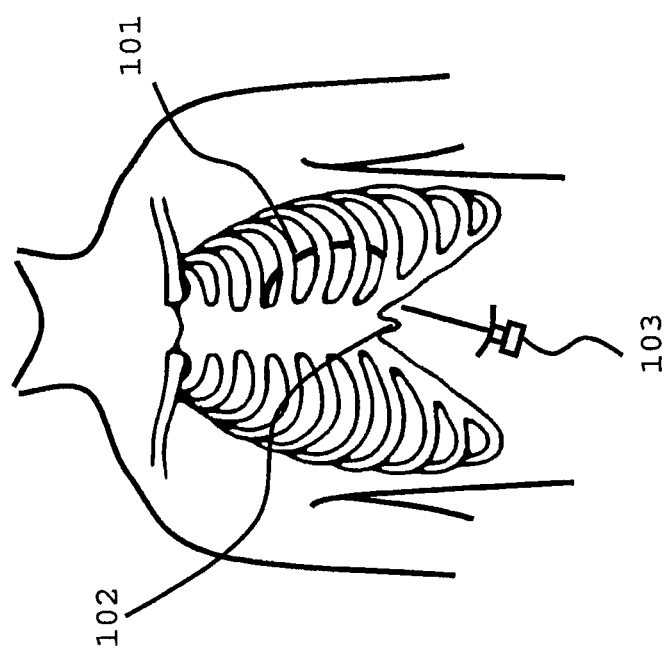

Conventionally, there are two commonly accepted locations on the chest that may be used for the insertion of a pericardial needle 103 to access the pericardial space 105: a) subxiphoid (FIGS. 1A and 2) and b) apical (FIG. 1B).

Figure 2:
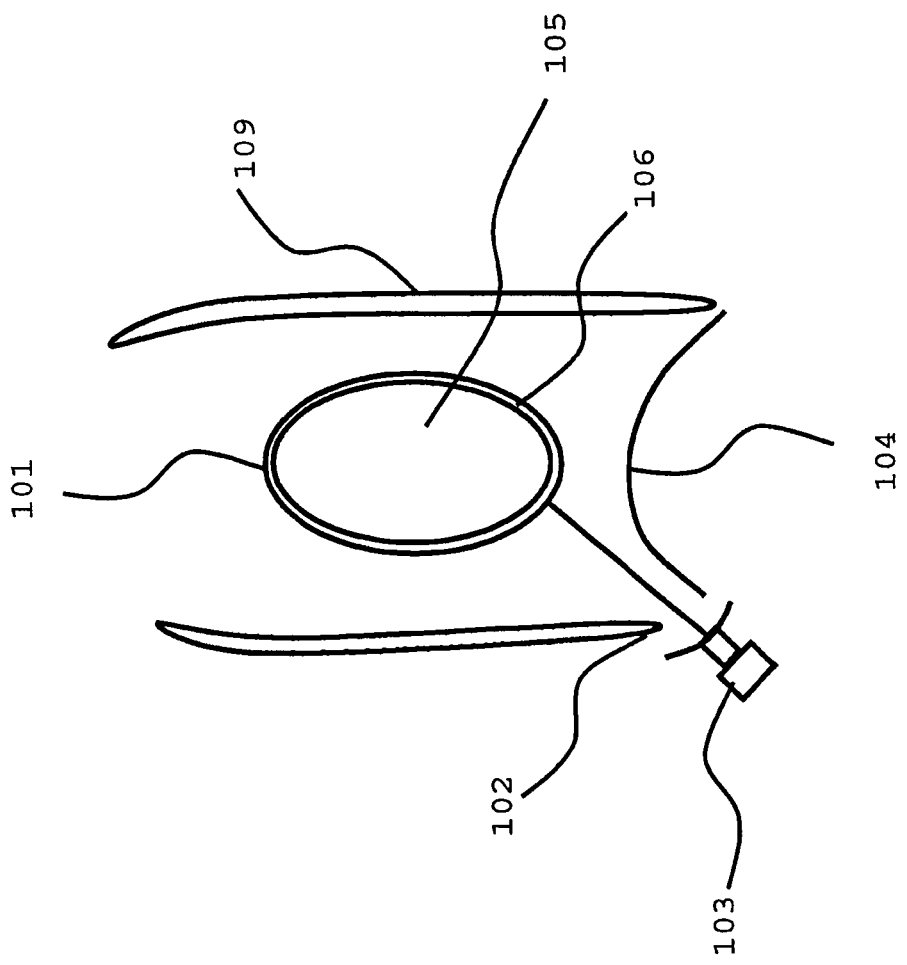
FIG. 2 is an exemplary side view illustration of an exemplary location on the chest that may be used for the insertion of a pericardial needle to access the pericardial space of the heart.

Although the apical location corresponds to a lower risk of damaging extra-cardiac structures, as not many exist in the needle's path, it is generally avoided due to the presence of a major coronary artery (the left Anterior Decending Coronary Artery) in the area where the puncture occurs, and hence the associated risk of puncturing that artery and causing a heart attack. Access into the pericardial space 106 is attained with a blunt tip needle 103 adopted from the field of anesthesia, called the Tuohy needle. The Tuohy needle is an epidural introducer needle. To use the subxiphoid location to access the pericardial space 106 between the heart muscle 105 and the parietal pericardium 101, the needle 103 is carefully inserted between the Xiphoid process 102 and the diaphragm 104, as illustrated in FIG. 2, and advanced toward the heart muscle 105 in order to penetrate the parietal pericardium 101 without damaging or penetrating the heart muscle 101. Human back ribs 109 are also illustrated in FIG. 2 for clarity.

Multiple advancements of the needle 103, with gradual increase in pressure applied to the parietal pericardium 101 may be required until it is punctured. In order to determine if/when the parietal pericardium 101 is punctured, test injections of a contrast agent may be done following each advancement. Once the parietal pericardium 101 is punctured, the contrast agent can be seen filling the pericardial space 106. At this point, no additional punctures are required/performed.

With the exception of patients with pericardial effusion (patients with large amount of fluid collection in the pericardial space due to bleeding or other disease process), the process of accessing the pericardial space 106 is difficult with a relatively high complication rate due to the small space between the parietal pericardium 101 and the heart muscle 105 (few millimeters at most) and the continuous motion of the heart before, during, and after puncturing the parietal pericardium 101.

In some cases, the needle tip may penetrate the heart muscle 105, creating a blood leak from the inside of the heart into the pericardial space 106. Such blood leak can lead to tamponade and hypotension. In other cases, the needle tip may damage a coronary artery (arteries that supply the heart muscle with oxygen and nutrients), which can cause a heart attack. Such complications are life threatening.

Other possible risks include damage to extra-cardiac structures that are present in the needle path. For example, the needle 103 may puncture the stomach, colon, liver, or diaphragm. It may also lacerate an artery causing significant bleeding. Such complications are serious, and potentially life threatening.

Figure 3:
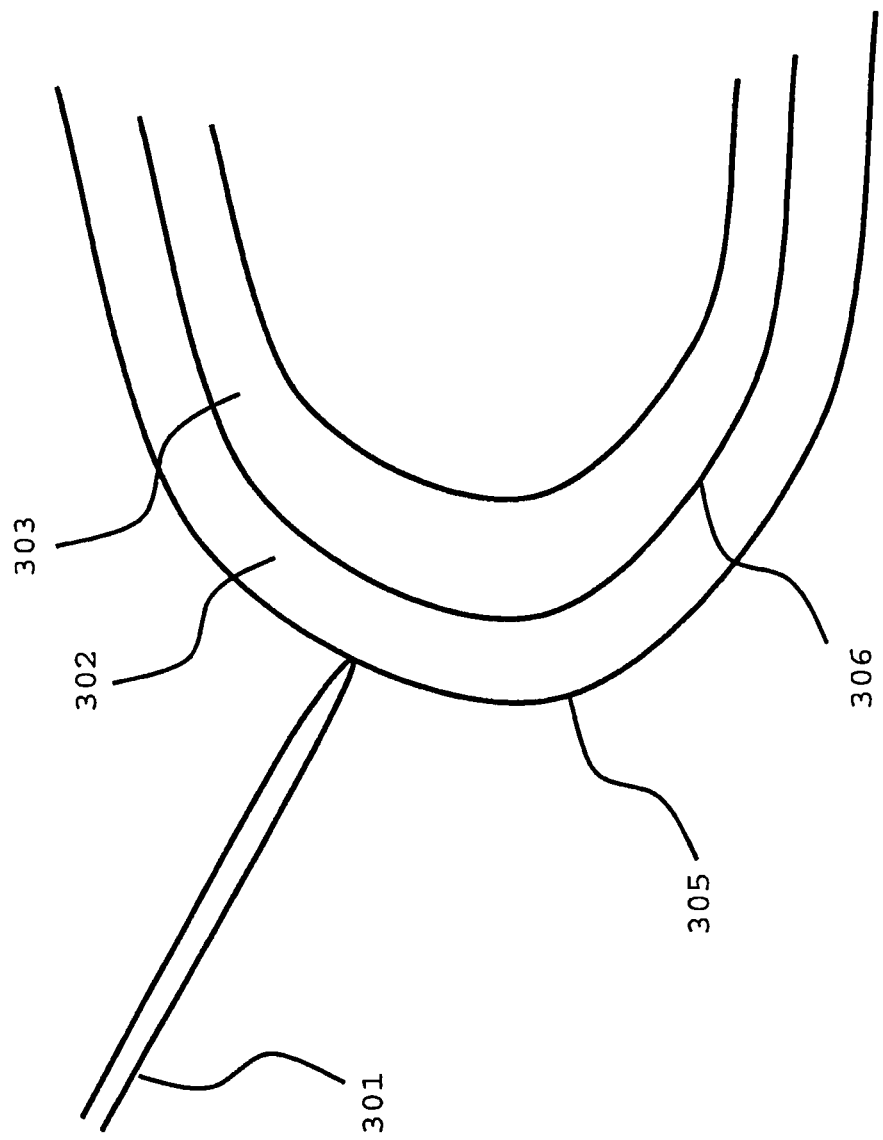
FIG. 3 is an exemplary cross-sectional illustrative view of accessing the pericardial space using a pericardial needle such that parietal pericardium, pericardial space, visceral pericardium, and myocardium are illustrated.

FIG. 3 is an illustrative view of a process for accessing the pericardial space 302 using a pericardial needle 301. Parietal pericardium 305, pericardial space 302, visceral pericardium 306, and myocardium 303 are illustrated in FIG. 3. The pericardial needle 301 must penetrate into the parietal pericardium 305 to access the pericardial space 302.

Figure 4:
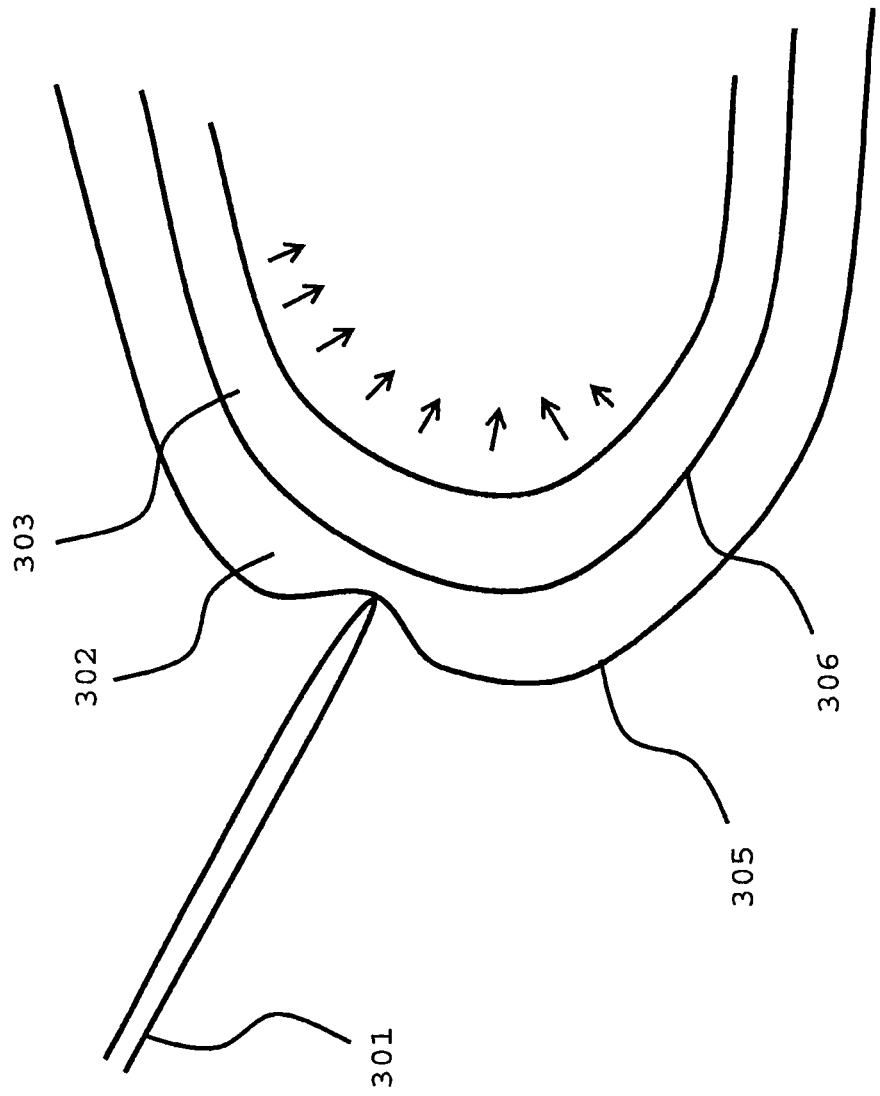
FIG. 4 is an exemplary cross-sectional illustrative view of a process for accessing the pericardial space when the heart is in systole.
Figure 5:
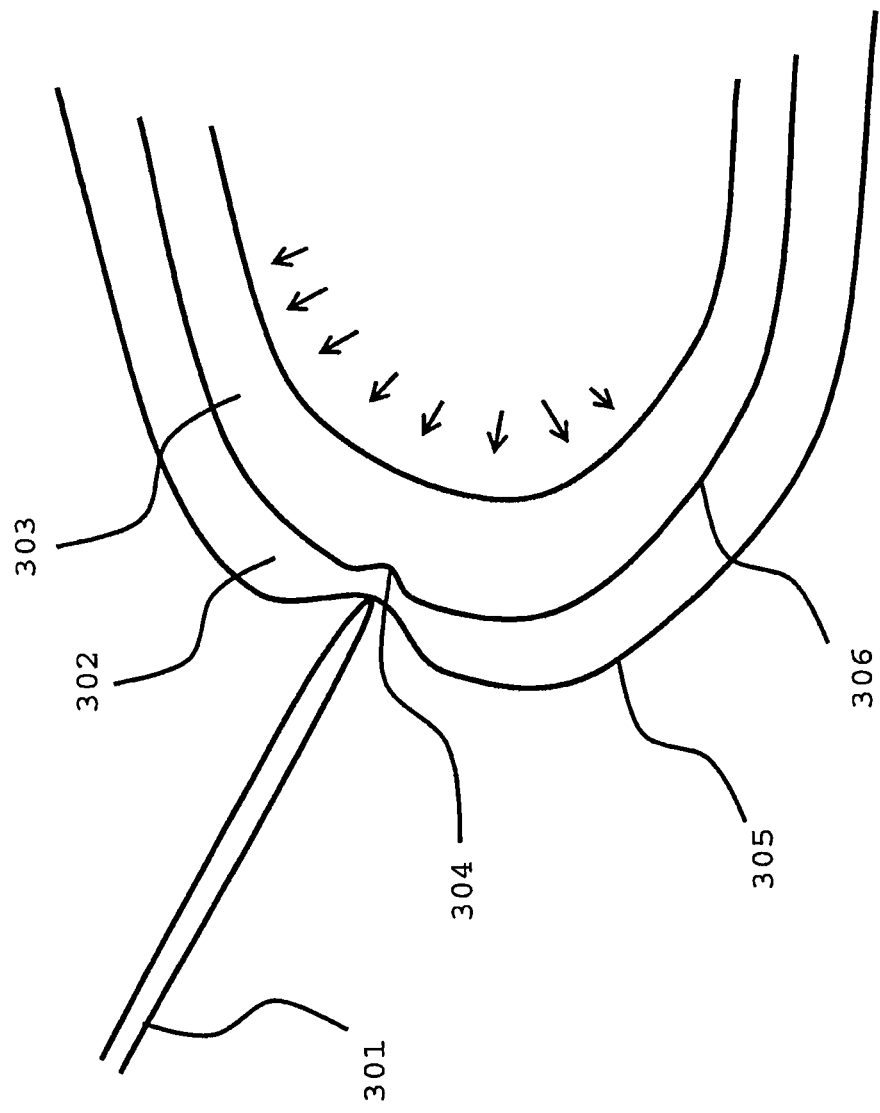
FIG. 5 is an exemplary cross-sectional illustrative view of a process for accessing the pericardial space when the heart is in diastole.

FIGS. 4 and 5 are illustrative views of a process of accessing the pericardial space 302 when the heart is in systole and diastole, respectively. The heart muscle or the myocardium 303 is in continuous motion. This motion is periodic and is called the cardiac cycle. The cardiac cycle is composed of two main phases called systole and diastole. Systole is the phase where the heart muscle 303 contracts, causing the heart to eject blood out of its inner cavities. Diastole is the relaxation phase during which the heart muscle 303 is relaxed and the heart chambers are filled with blood.

As the needle 301 advances towards the pericardial space 302, the motion of the heart muscle 303 has significant impact on the ability to achieve the goal of penetrating the parietal pericardium 305, without penetrating or damaging the adjacent moving heart muscle 303.

The inventor of the present disclosure identified that the risk of inadvertently penetrating the heart muscle 303 is significantly lower if the penetration of the parietal pericardium 305 is synchronized with the movement of the heart. This is due to the fact that the heart muscle 303 is moving away from the needle 301 during systole as shown in FIG. 4. Thus, the disclosed methods of the present disclosure take advantage of the motion of the heart muscle 303, and change this motion from a factor that adds to the risk of the procedure, to one that helps attain safer access to the pericardial space 302. That is, a puncture of the pericardium may be synchronized with the motion of the heart.

The parietal pericardium 305 encases the heart muscle 303. The distance between the parietal pericardium 305 and the outer layer of the heart muscle 303 (the visceral pericardium 306) changes slightly as the heart muscle 303 moves. This change in the distance between the parietal pericardium 305 and the heart muscle 303 provides a time window of opportunity for a safer access to the pericardial space 302, when such access is synchronized with the movement of the heart muscle 303.

FIGS. 4 and 5 illustrate the indentation of the parietal pericardium 305 while the needle 301 (e.g., a cautery needle) is held in a fixed position. That is, the indentation of the parietal pericardium 305 is the same in systole and diastole, while on the heart muscle 303 there is no indentation (tenting) in systole, but some minor indentation exists in diastole.

According to an embodiment of the present disclosure, accessing the pericardial space 302 may be achieved by advancing the pericardial needle 301 through the parietal pericardium 305 in brief pulses, and synchronizing these pulses to systole where the heart muscle 303 contracts, thereby moving away from the needle 301. As the needle tip is advanced and in contact with the pericardial membrane, brief pulses of energy (e.g., electrical, laser, pressure, radiofrequency) are timed with the movement of the heart so that the puncture of the pericardium and the advancement of the needle through the pericardial membrane is timed or synchronized with the systole or diastole. In other words, accessing the pericardial space 302 may be achieved by advancing the pericardial needle 301 through the parietal pericardium 305 when the heart muscle 303 contracts (systole) thereby moving away from the needle 301 with an energy pulse corresponding with the peak of movement away from the cautery needle. This method can also be applied when the heart muscle is in rest in a static condition.

Cautery is a process by which tissue can be cut or coagulated. High frequency alternating current is applied to tissue through a metal probe resulting in heat, which destroys that tissue. It can be delivered in unipolar or bipolar fashion. In unipolar type, energy is delivered to tissue with a metal probe (active electrode) and exits through a patch placed on the body with a large surface area (indifferent plate). The highest current density is at the smallest area of the circuit which is at the tip of the probe, and that's where heating and tissue destruction occurs. Continuous current results in "cutting" while intermittent current results in coagulation. In bipolar cautery, a circuit is established between two probe tips in contact with tissue. Heating and tissue destruction occurs between the two tips.

According to an embodiment of the present disclosure, accessing the pericardial space 302 may be achieved by inserting the pericardial needle 301 between the ribs at the left side of the chest. Although, important coronary arteries may exist in such location, the associated risk of inadvertently puncturing a coronary artery is reduced due to the synchronization of the needle advancement with the movement of the heart muscle 303, thereby making this location a viable option for using in the process of accessing the pericardial space 302.

In order to detect and synchronize with systole, visual, mechanical, electrical, or any similar measurement indicative and/or predictive of systole, diastole and/or the heart condition may be utilized. For example, according to an embodiment of the present disclosure, an echocardiogram may be used by a physician performing the process, to visually monitor the motion of the cardiac muscle.

Figure 6:
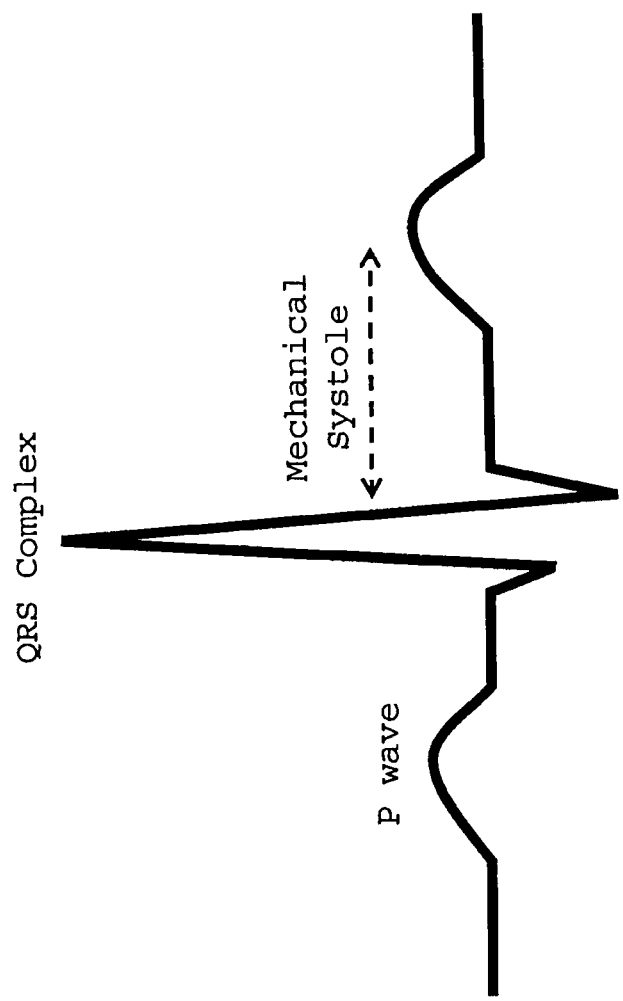
FIG. 6 is an exemplary graph of an electrocardiogram.

According to another embodiment of the present disclosure, an electrocardiogram (ECG) may be utilized to indicate the phase of the cardiac cycle, and synchronize with systole. FIG. 6 is a graph of an ECG, which is a recording of the electrical activity of the heart. A typical and exemplary ECG of the cardiac cycle (heart beat) consists of a P-wave, a QRS complex, and a T-wave. The P-wave reflects the atrial activation. The QRS complex reflects the ventricular activation, which is the electrical activity that causes the ventricular heart muscle 303 to contract. Accordingly, the actual systolic mechanical motion of the ventricles shortly follows the onset of the QRS complex shown in the ECG in FIG. 6.

Typically, mechanical systole starts approximately 30-40 msec after the QRS onset (e.g., beginning of the Q wave), and lasts for approximately 250-350 msec at resting heart rate in normal hearts. The duration of systole and the time between the onset of the QRS and the beginning of systole may be altered by, for example, the heart rate, age, gender, body mass index (BMI), and/or the presence of heart disease in a human patient.

According to an embodiment of the present disclosure, the needle 301 may puncture the pericardial membrane with a cautery pulse preferably any time after the beginning, and before the end of systole. According to an embodiment, a brief cautery pulse may be delivered within a time window of, for example, 300 msec, starting at, for example, 50 msec after the QRS and ending at, for example, 150 msec after the QRS.

According to another embodiment of the present disclosure, the time window allowed for cautery pulse (and needle puncture) may be adjusted based on one or more of many contributing factors including the heart rate, age, gender, and BMI of a patient, in addition to the presence and nature of underlying heart disease. Such adjustment may be in terms of a percentage of the time window. Such adjustment may be manually performed by the physician performing the process of puncturing the parietal pericardium 305, or may be automatically performed by a controller. Lab testing may be used to search for the best time interval during the cardiac cycle and/or during systole.

Figure 7:
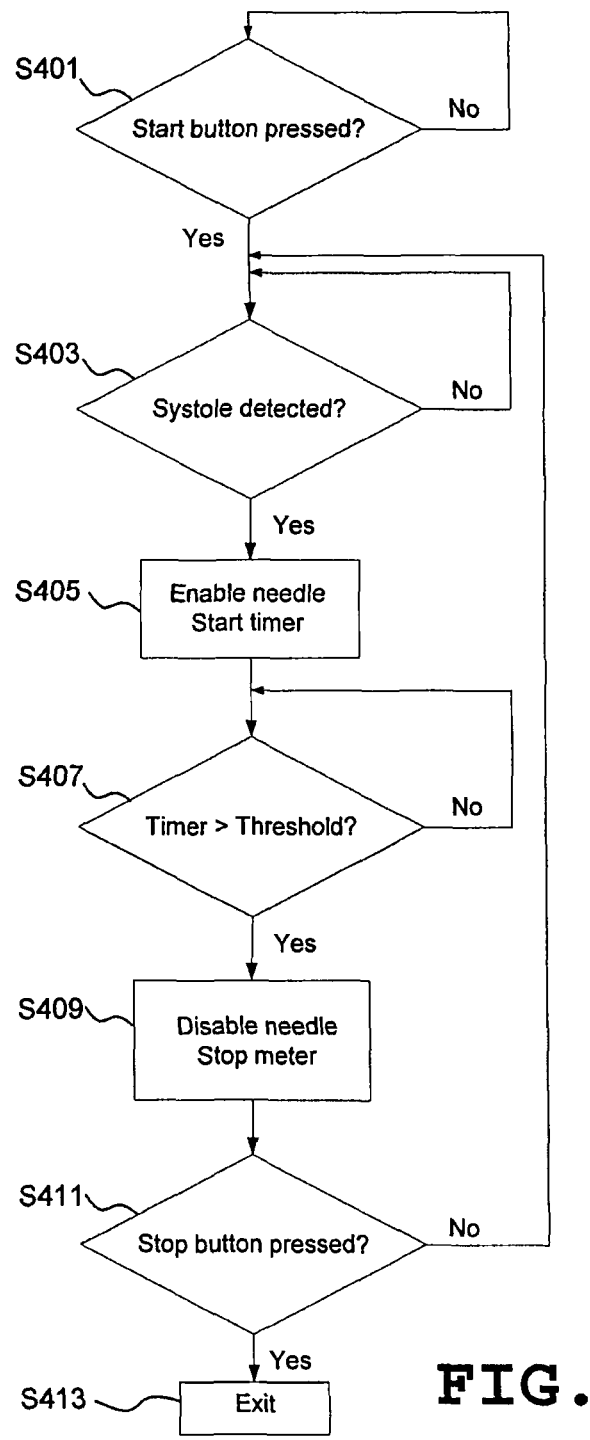
FIG. 7 is an exemplary flowchart for an embodiment of a method for synchronizing the process of accessing the pericardial space with the heart's systole using a pericardial needle.

FIG. 7 is a flowchart for an exemplary embodiment of a method for synchronizing the process of accessing the pericardial space 302 with the heart's systole using different embodiments of the pericardial needles 103, 301, 650, and/or 660 as disclosed in this application. In step S401, the process determines whether an instruction for initiation of the process has been given. For example, a start button may be pressed by a physician, indicating the initiation of the process of accessing the pericardial space 302. If no indication of initiation has been detected, the process loops back to step S401. Otherwise, the process proceeds to step S403.

In step S403, the process checks if systole is detected. Detection of systole may be according to visual, mechanical, electrical, or any other measurement indicative of systole. If systole is not detected, the process loops back to step S403. Otherwise, the process proceeds to step S405.

In step S405, the needle 301 is enabled and a timer is started. According to an embodiment, a cautery needle, previously held in a disabled state, may be enabled in step S405, such that the cautery needle punctures the parietal pericardium 305 when cautery is enabled. According to another embodiment, a needle blade, previously held in a secured state, may be released in step S405, such that the needle blade punctures the parietal pericardium 305 when released. According to another embodiment, a laser needle, previously held in an inactive state, may be activated in step S405, such that the laser needle punctures the parietal pericardium 305 when activated. According to another embodiment, a pressure needle, previously held in an inactive state, may be activated in step S405, such that the pressure needle delivers a short burst of high-pressure fluid and punctures the parietal pericardium 305 when activated.

In step S407, the process checks if the timer has exceeded a predetermined threshold. The predetermined threshold may be set according to an estimate of the duration of systole from previous measurements. If the timer has not exceeded a predetermined threshold, the process loops back to step S407. Otherwise, the process proceeds to step S409.

In step S409, the needle 301 is disabled and the timer is stopped. According to an embodiment, a cautery needle is disabled in step S409, such that cautery is no longer deliverable, so that the needle does not punctures the parietal pericardium 305 when disabled. According to another embodiment, a needle blade is secured in step S409, such that the needle blade does not puncture the parietal pericardium 305 when secured. According to another embodiment, a laser needle is de-activated in step S409, such that the laser needle does not puncture the parietal pericardium 305 when de-activated.

In step S411, the process checks if an instruction to stop needle advancement and/or stop the process has been received. For example, a stop button may be pressed by a physician, indicating the success and/or termination of the process of accessing the pericardial space 302. If the process has not been interrupted, the process loops back to step S403. Otherwise, the process exits in step S413.

Multiple advancement toward the parietal pericardium 305 and application of cautery may be required in order to successfully puncture the pericardial membrane. A physician may determine the success of puncturing the parietal pericardium 305 by monitoring the operation and looking for the indication that a test contrast agent injection flows into the pericardial space 302 as observed under fluoroscopy imaging. As previously mentioned, detection of systole may be according to visual, mechanical, electrical, or any other measurement indicative of systole.

Figure 8:
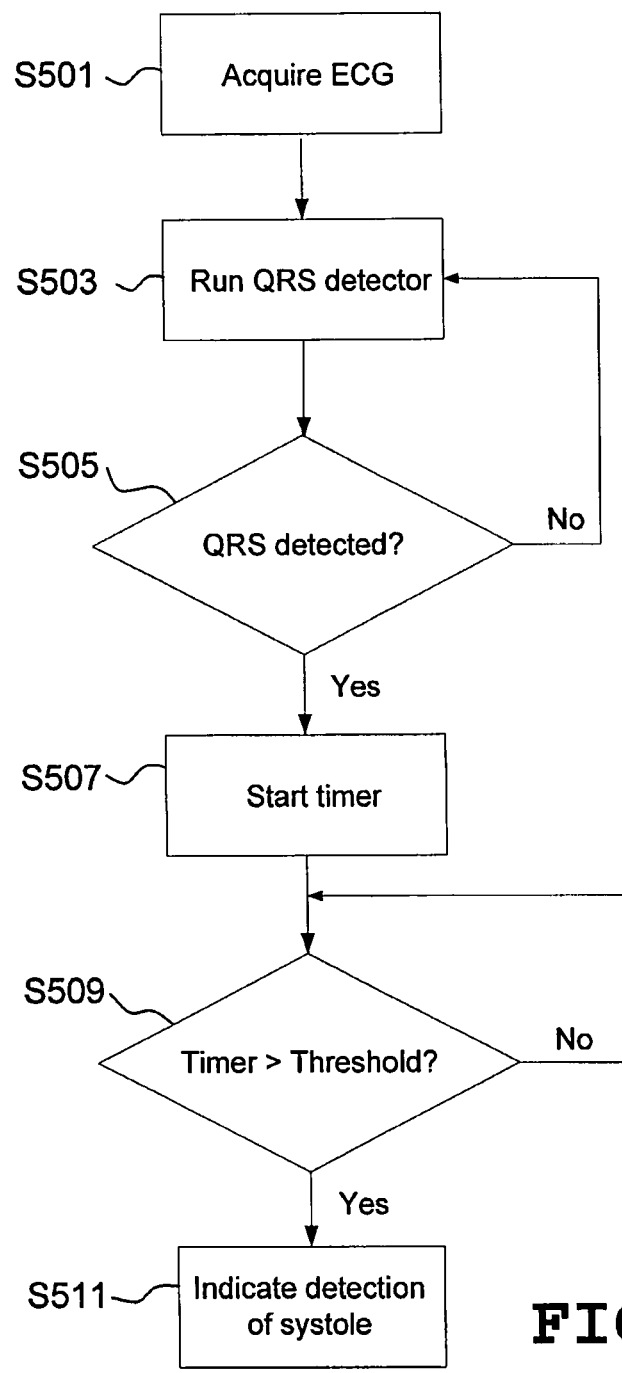
FIG. 8 is an exemplary flowchart for an embodiment of a method for detecting systole based on an electrocardiogram.

FIG. 8 is a flowchart for an embodiment of a method for detecting systole based on the ECG. In step S501, ECG is acquired. According to an embodiment, ECG may be acquired according to a conventional method, for example, via ECG electrodes, followed by ECG instrumentation and signal processing. According to another embodiment, acquisition of ECG may be performed according to conventional ECG electrodes, followed by, for example, ECG instrumentation and signal processing, and wireless transmission of the ECG signals to a controller. According to an embodiment, acquisition of ECG may be according to conventional ECG electrodes, followed by, for example, ECG instrumentation and signal processing, and fiber optic transmission of the ECG signals to a controller.

In step S503, a QRS detector is run. According to an embodiment, detection of QRS may be according to a conventional method of slope detection. According to another embodiment, detection of QRS may be according to an envelope or template detection. The envelope or template detection may be according to a previously acquired QRS, or according to a standard QRS profile or template. The standard QRS profile or template may be adjustable according to one or more of an age, gender, BMI, or heart rate of a human patient.

According to another embodiment, detection of QRS may be according to an extremum detection, such as an R-wave peak detection, a Q-wave minimum detection, or an S-wave minimum detection. Alternatively, detection of QRS may include detection of a sequence of extremums, e.g., a Q-wave minimum followed by an R-wave peak, or an R-wave peak followed by an S-wave minimum.

Detection of QRS may be performed in real-time, and with tolerable delay, such that the detected QRS corresponds to the mechanical activity of the heart in real-time. The tolerable delay between the onset of the QRS complex and the detection of the QRS complex may depend on the duration of systole, and/or the time period between the onset of the QRS complex and systole.

In step S505, the process checks if QRS is detected. If QRS is not detected, the process loops back to step S505. Otherwise, the process proceeds to step S507.

In step S507, a timer is started to measure the time elapsed since the detection of QRS.

In step S509, the process checks if the timer has exceeded a predetermined threshold. The predetermined threshold may be set according to an estimate of the duration of time between the detection of QRS and systole. If the timer has not exceeded the predetermined threshold, the process loops back to step S509. Otherwise, the process proceeds to step S511.

According to an embodiment, the predetermined threshold may be adjustable according to one or more of an age, gender, BMI, presence of underlying heart disease, or heart rate of a human patient.

In step S511, detection of systole is indicated. Alternatively, other similar methods may be used to indicate systole. According to an embodiment of the present disclosure, a pressure measurement may be used to synchronize the process of accessing the pericardial space 302 with systole. The pressure measurement may be performed at the tip of the needle 301 or at the tip of a further optional needle such as a contrast needle. Alternatively, arterial pressure wave, through an arterial line, or pulse oximetery wave (Plethysmograph) may be used.

The arterial blood pressure indicative of systole may be determined by the measurement of the arterial blood pressure before the process of puncturing the parietal pericardium, and adjusting the expected arterial blood pressure during systole either manually or automatically. As the arterial blood pressure is subject to variation, such measurement may be monitored continuously, updated continually or from time to time, for example, 1, 10, 100 milliseconds, or 1, 10, 100 milliseconds, during the process of puncturing the parietal pericardium.

Figure 9:
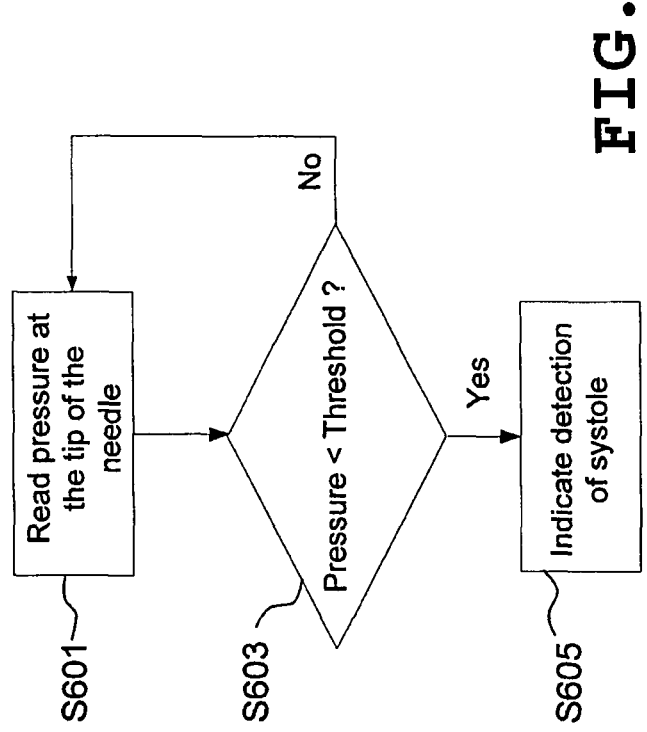
FIG. 9 is an exemplary flowchart for an embodiment of a method for detecting systole based on a pressure measurement at the tip of a pericardial needle.

FIG. 9 is a flowchart for an embodiment of a method for detecting systole based on a pressure measurement at the tip of the needle 301. In step S601, a pressure measurement is made at the tip of the needle 301. In step S603, the process checks if pressure has fallen below a predetermined threshold. The predetermined threshold may be set according to an estimate of the pressure expected at the tip of the needle 301 during systole. If the pressure has not fallen below the predetermined threshold, the process loops back to step S603. Otherwise, the process proceeds to step S605. The predetermined threshold may be adjustable according to one or more of an age, gender, BMI, or heart rate of a human patient. In step S605, detection of systole is indicated.

Figure 10:
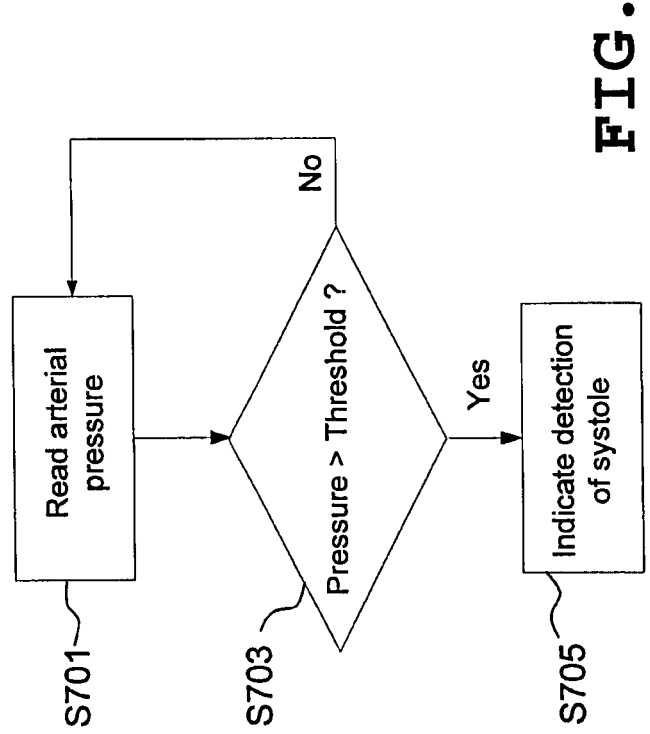
FIG. 10 is an exemplary flowchart for an embodiment of a method for detecting systole based on arterial pressure measurement.

FIG. 10 is a flowchart for an embodiment of a method for detecting systole based on arterial pressure measurement. In step S701, an arterial pressure wave is detected. The detection of the arterial pressure wave may be through an arterial line, or pulse oximetery wave (Plethysmograph). In step S703, the process checks if the arterial pressure has exceeded a predetermined threshold. The predetermined threshold may be set according to an estimate of the arterial pressure during systole. If the arterial pressure has not exceeded a predetermined threshold, the process loops back to step S703. Otherwise, the process proceeds to step S705. The predetermined threshold may be adjustable according to one or more of an age, gender, BMI, presence of underlying heart disease, or heart rate of a human patient. In step S705, detection of systole is indicated.

Figure 11:
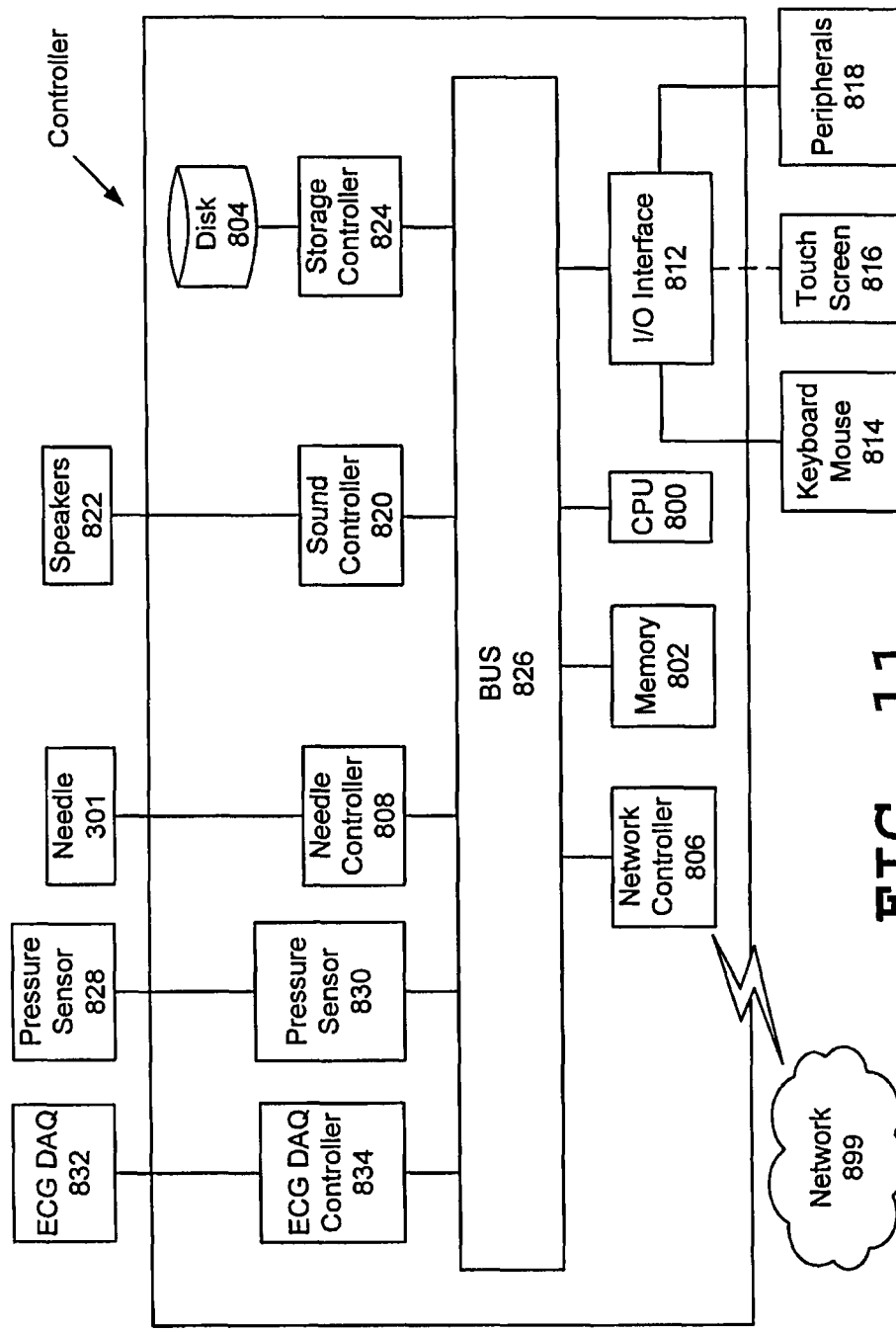
FIG. 11 is an exemplary block diagram of a controller for controlling a pericardial needle that punctures the pericardial membrane by synchronizing energy delivery/needle advancement with cardiac muscle motion.

FIG. 11 is a block diagram of a controller, which may be used to perform the above-described processes. A hardware description of the controller according to exemplary embodiments is described with reference to FIG. 11. The pericardial needle or the needle 301 of the FIG. 11 can be any of the different embodiments of the pericardial needles as disclosed in this application, preferably a cautery needle.

In FIG. 11, the controller includes a CPU 800 which may be used to perform the processes described in the present disclosure. The process data and instructions corresponding to the processes described in the present disclosure may be stored in memory 802. These processes and instructions may also be stored on a storage medium disk 804 such as a hard drive (HDD) or portable storage medium or may be stored remotely.

Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the controller communicates, such as a server or computer.

Further, the claimed advancements may be provided as a utility application, background daemon, or component of an operating system, or combination thereof, executing in conjunction with CPU 800 and an operating system such as Microsoft Windows 7, UNIX, Solaris, LINUX, Apple MAC-OS and other systems known to those skilled in the art.

CPU 800 may be a Xenon or Core processor from Intel of America or an Opteron processor from AMD of America, or may be other processor types that would be recognized by one of ordinary skill in the art. Alternatively, the CPU 800 may be implemented on an FPGA, ASIC, PLD or using discrete logic circuits, as one of ordinary skill in the art would recognize. Further, CPU 800 may be implemented as multiple processors cooperatively working in parallel to perform the instructions of the inventive processes described in the present disclosure.

The controller in FIG. 11 also includes a network controller 806, such as an Intel Ethernet PRO network interface card from Intel Corporation of America, for interfacing with network 899. As can be appreciated, the network 899 can be a public network, such as the Internet, or a private network such as an LAN or WAN network, or any combination thereof and can also include PSTN or ISDN sub-networks. The network 899 can also be wired, such as an Ethernet network, or can be wireless such as a cellular network including EDGE, 3G and 4G wireless cellular systems. The wireless network can also be WiFi, Bluetooth, or any other wireless form of communication that is known.

The controller further includes a display controller 808, such as a NVIDIA GeForce GTX or Quadro graphics adaptor from NVIDIA Corporation of America for interfacing with display 810, such as a Hewlett Packard HPL2445w LCD monitor. A general purpose I/O interface 812 interfaces with a keyboard and/or mouse 814 as well as a touch screen panel 816 on or separate from display 810. General purpose I/O interface also connects to a variety of peripherals 818 including printers and scanners, such as an OfficeJet or DeskJet from Hewlett Packard.

A sound controller 820 is also provided in the controller, such as Sound Blaster X-Fi Titanium from Creative, to interface with speakers/microphone 822 thereby providing sounds and/or music. The speakers/microphone 822 can also be used to accept dictated words as commands for controlling the controller or for providing location and/or property information with respect to the target property.

The general purpose storage controller 824 connects the storage medium disk 804 with communication bus 826, which may be an ISA, EISA, VESA, PCI, or similar, for interconnecting all of the components of the controller. A description of the general features, detail features, and functionality of the display 810, keyboard and/or mouse 814, as well as the display controller 808, storage controller 824, network controller 806, sound controller 820, and general purpose I/O interface 812 is omitted herein for brevity as these features are known.

An ECG data acquisition (DAQ) controller 834 is also provided in the controller, to interface with an ECG DAQ 832, so an ECG measurement may be controlled, displayed and/or recorded via the controller, and used in a process of accessing the pericardial space 302.

A pressure sensor controller 830 is also provided in the controller, to interface with a pressure sensor 828, so a pressure measurement may be controlled, displayed and/or recorded via the controller. The pressure measurement may be used in a process of accessing the pericardial space 302.

A needle controller 808 is also provided in the controller, to interface with the needle 301, so the needle 301 may be controlled via the controller.

In a preferred embodiment, during use the pericardial needle is advanced to the pericardial membrane so that the tip 606 is directly adjacent and in contact with the pericardial membrane. Sufficient pressure is applied to the needle so that the pericardial membrane is indented. A relatively blunt tip is preferred to avoid unintentional cut or damage to the pericardial membrane. The needle has a lumen that connects to a sidearm at the base of the needle. The sidearm is connected to a source containing contrast solution. The contrast solution fills the lumen of the needle. The fluid is under pressure but does not escape through the blunt tip of the needle, which is obstructed by contact with the pericardial membrane.

Upon administration of a cautery pulse to the cautery needle the pericardial membrane may be cut and/or punctured. The puncture of the pericardial membrane leads to advancement of the pericardial needle into the pericardial space. Entry of the needle into the pericardial space exposes the needle tip to a different pressure environment, i.e., the pressure on the contrast fluid in the needle decreases upon entry of the needle into the pericardial space. The change in pressure results in release of contrast fluid from the needle tip into the pericardial space.

During advancement of the pericardial needle (cautery needle) the presence of contrast agent may be monitored by fluoroscopy. Although small amounts of contrast fluid may escape from the contrast needle prior to entry of the contrast needle into the pericardial space due to an imperfect seal between the needle tip and the pericardial membrane, the amount of contrast fluid released upon cutting or penetration of the pericardial membrane results in the release of a substantial amount of contrast agent which is immediately evident by fluoroscopy. This will alert the operator to the needle puncturing the pericardial membrane, and no further cautery or needle advancement is necessary.

The contrast solution can be contained in a pressurized syringe connected to the sidearm. The pressure can be adjusted. While the needle tip is being advanced through tissue or resting against the pericardial membrane, the existing pressure is not sufficient to push contrast through the tip and into surrounding tissue. Once the tip punctures the pericardial membrane, and is in the lower pressure pericardial space, the pressure drop at the needle tip allows forward flow of the contrast agent into the pericardial space. Alternatively, the supply of contrast fluid to the needle may be controlled by the controller. Upon entry into the pericardial space the reduction in pressure in the contrast needle may result in a large dose of contrast agent delivered to the pericardial space. The controller may act to minimize or stop the flow of contrast agent upon detection of a pressure change in the contrast needle.

Subsequent to entry of the pericardial needle into the pericardial space, the needle may be withdrawn. In one embodiment, a wire is inserted through a valve at the base of the needle. The wire goes through the tip of the needle and the distal end of the wire is placed in the pericardial space. The proximal end of the wire remains outside the body and outside the needle. The needle is pulled out "over the wire" while the wire remains in place. Inserting a wire through a needle into the compartment of interest then removing the needle "over the wire" is common medical practice when attempting to gain access to various areas of the body. This allows for a sheath (a tube with a valve at the operators end) to be inserted over the wire into the pericardial space. A sheath functions as a direct communication into the pericardial space. Medical agents, drugs, ablation catheters, pacing leads, and other instruments can be inserted into the pericardial space through a sheath.

In another embodiment the pericardial needle includes a first lumen and a second lumen. The first lumen may connect, for example, to contrast source and the second lumen may contain, for example, a wire or other apparatus for treating, measuring, contacting the pericardial membrane, or allow for easy advancement of the cautery needle through skin and other tissue prior to reaching the pericardial membrane. A sharp tip "stylet" may be placed through one lumen where the tip of the stylet extends beyond the cautery needle tip and helps advance the assembly through tissue given the relatively blunt tip of the cautery needle.

The disclosed methods make access into the pericardial space 302 easier and safer by utilizing the cardiac motion to puncture the parietal pericardium in synchronization with the cardiac motion.

The disclosed methods may be used to gain access into the pericardial space 302 in order to deliver drugs to the heart muscle and/or the coronary arteries. Since the pericardial fluid is of relatively low volume, delivering drugs via the pericardial fluid requires a relatively lower dose of drug. Additionally the disclosed methods may be used to access into the pericardial space 302 in order to introduce an agent into the pericardial space 302, thereby localizing the agent to the area around the heart muscle. Such agent is thereby contained within the pericardial fluid, without contaminating other tissue or parts. Also, due to the low turn over rate of the pericardial fluid, such agent is sustained over a longer period of time.

The disclosed methods may be used to gain access into the pericardial space 302 in order to insert a cathether to deliver drugs and/or agents. The disclosed methods may be used to gain access into the pericardial space 302 in order to insert a cathether to collect biological tissue or cells.

The disclosed methods may be used to access the pericardial space 302 in order to insert a cathether to perform ablation of arrhythmia. A catheter is inserted into the pericardial space 302 to target a specific area of the heart. Ablation of arrhythmia is performed by directing energy through a catheter to small areas of the heart muscle that cause abnormal heart rhythm, to disconnect the source of the abnormal rhythm from the rest of the heart. This process may also be used to disconnect abnormal electrical pathways between the atria and the ventricles.

The disclosed methods may be used to access the pericardial space 302 in order to insert a cathether or tool to ligate the left atrial appendege. The disclosed methods may be used to access into the pericardial space 302, in order to introduce implantable defibrillator and/or pacemaker electrodes into the pericardial space 302.

Figure 12A:
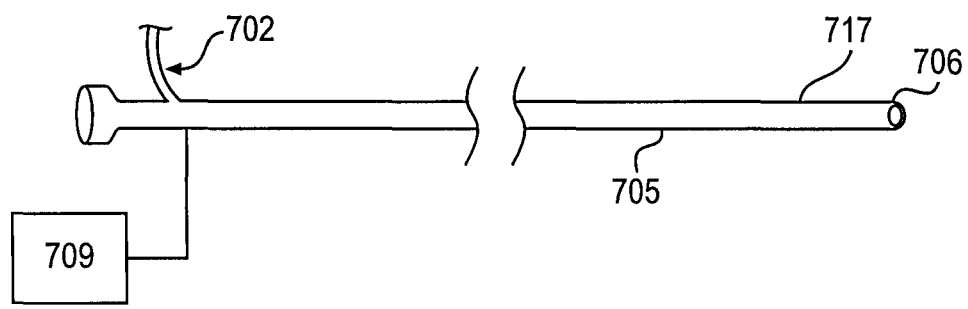
FIG. 12a is an exemplary cross-sectional illustrative view of a cautery pericardial needle that punctures the pericardial membrane by synchronizing energy delivery (cautery pulse) with cardiac muscle motion in a baseline position.

FIG. 12a is an exemplary cross-sectional illustrative view of a cautery pericardial needle 760 that punctures the pericardial membrane by synchronizing cautery impulses with cardiac muscle motion. The pericardial needle 760 has an cautery needle 717 with a relatively blunt tip 706. The needle is preferably partially sheathed with a non-conductive coating that restricts energy exit through the tip 706. The needle has one or more lumens 705. The lumen 705 can be used to insert a stylet with a sharp tip to help advance the needle through tissue. The lumen can also be used inject contrast through a sidearm to confirm pericardial puncture, and to insert a wire into the pericardial space after puncture is confirmed.

The cautery needle 716 can provide rapid and brief cautery pulses when close to/in contact with the pericardial membrane. These pulses can be controlled by a controller 609. During contact of the cautery tip 706 with the pericardial membrane the controller 609 administers a cautery pulse to puncture or cut the pericardial membrane. For example, the puncture can be synchronized with systole.

Contrast may be injected through an inlet 702 of the lumen 705 with test injections done after or during each administration of cautery or puncture. Once the pericardium is punctured, contrast is seen filling the pericardial space. At this point, no additional punctures or cautery are done. A wire is optionally advanced into the pericardial space. The wire may be used as a guide for inserting a sheath into the pericardial space.

The controller 709 is configured to administer a pulse of energy (high frequency alternating current) to the cautery needle. When the energy is electrical energy the controller may administer a single short pulse or a plurality of short pulses of electrical energy to the cautery needle. This energy exits at the needle tip which is positioned against the pericardial membrane, and thus penetrating it. The controller may be programmed such that administration of the electrical pulse is automatic and is triggered by detection of the heart phase or alternately may be administered manually through a human operator triggering the pulse by command to the controller.

Figure 12B:
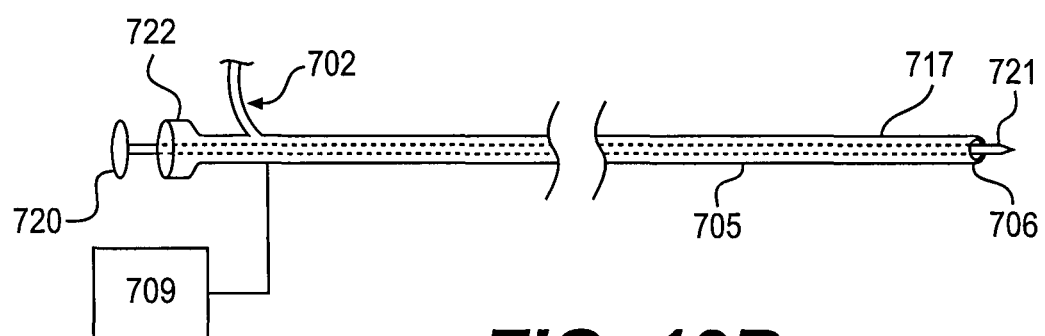
FIG. 12b is an exemplary cross-sectional illustrative view of a cautery pericardial needle that punctures the pericardial membrane by synchronizing energy delivery (cautery pulse) with cardiac muscle motion in a baseline position and contains a stylet.

FIG. 12b is an exemplary cross-sectional illustrative view of a cautery pericardial needle 760 that punctures the pericardial membrane by synchronizing cautery impulses with cardiac muscle motion. The pericardial needle 760 has an outer cautery needle 717 with a relatively blunt tip 706. The outer needle is preferably partially sheathed with a non-conductive coating that restricts energy exit through the tip 706. The needle has one or more lumens 705. The lumen 705 can be used to insert a stylet 720 with a sharp tip 721 to help advance the needle through tissue. The stylet 720 may be inserted in the lumen 705 through a valve 722 located at an end of the needle 717 opposite the blunt tip 706. The lumen 705 can also be used inject contrast through a sidearm to confirm pericardial puncture, and to insert a wire into the pericardial space after puncture is confirmed.

Preferably the cautery needle 717 is mechanically advanced, with the stylet 720 in the needle lumen 705, until the tip 721 is close to the pericardial membrane. The stylet 720 is then removed and the blunt cautery needle tip 706 is advanced further until it is in direct contact with the pericardial membrane.

The cautery needle 717 can provide rapid and brief cautery pulses when close to/in contact with the pericardial membrane. These pulses can be controlled by the controller 709. During contact of the cautery tip 706 with the pericardial membrane the controller 709 administers a cautery pulse to puncture or cut the pericardial membrane. For example, the puncture can be synchronized with systole.

The controller is configured to administer a pulse of energy (high frequency alternating current) to the cautery needle. When the energy is electrical energy the controller may administer a single short pulse or a plurality of short pulses of electrical energy to the cautery needle. This energy exits at the needle tip which is positioned against the pericardial membrane, and thus penetrating it. The controller may be programmed such that administration of the electrical pulse is automatic and is triggered by detection of the heart phase or alternately may be administered manually through a human operator triggering the pulse by command to the controller.

Figure 13:
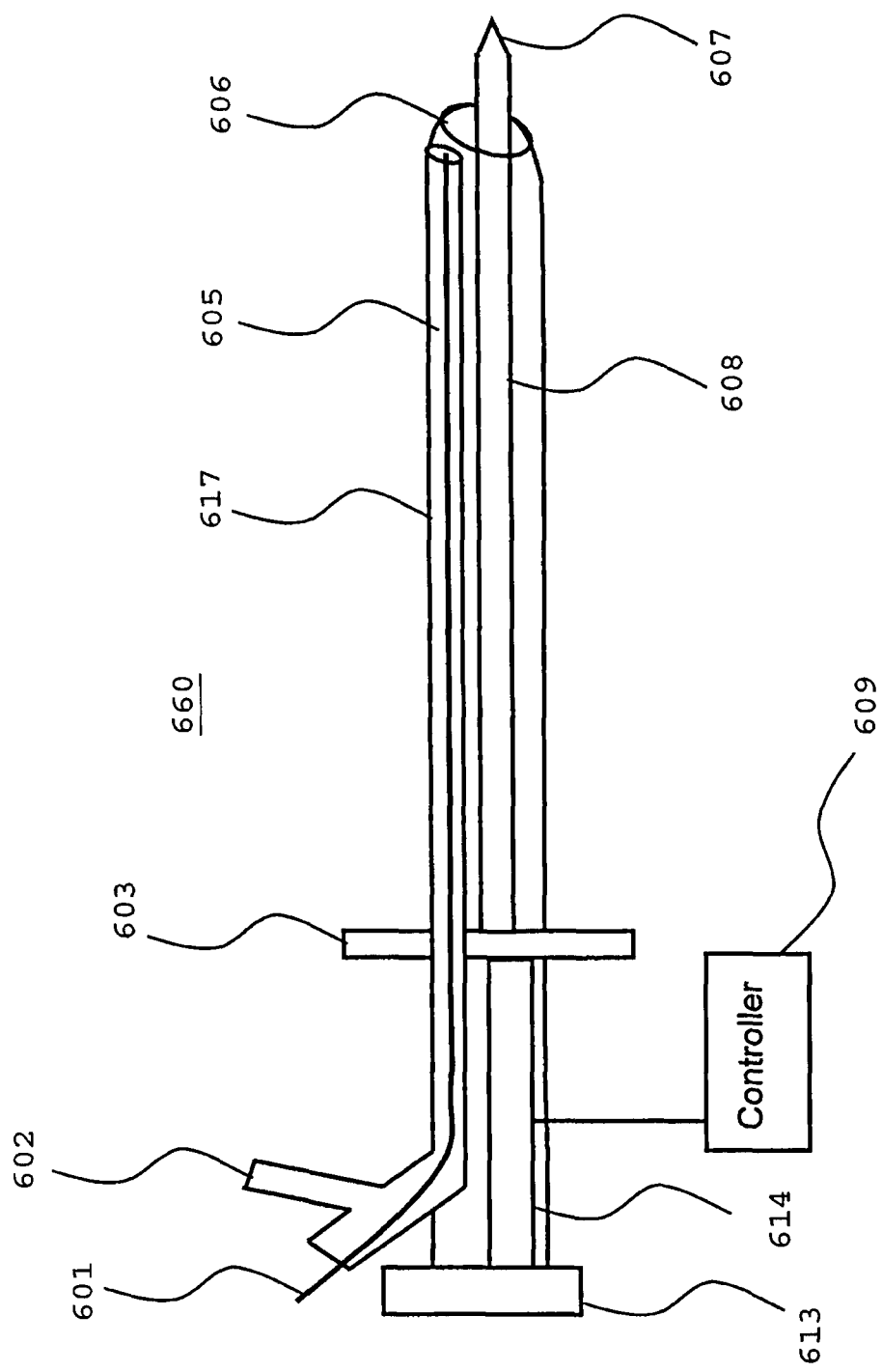
FIG. 13 is an exemplary cross-sectional illustrative view of a cautery pericardial needle with optional lumen that punctures the pericardial membrane by synchronizing energy delivery (cautery pulse) with cardiac muscle motion in a baseline position.

FIG. 13 is an exemplary cross-sectional illustrative view of a cautery pericardial needle 660 that punctures the pericardial membrane by synchronizing cautery impulses with cardiac muscle motion.

The pericardial needle 660 has an outer cautery needle 617 with a relatively blunt tip 606. The outer needle is preferably partially sheathed with a non-conductive coating that restricts energy exit through the tip 606. The needle has one or more lumens. The lumen can be used to insert a stylet with a sharp tip to help advance the needle through tissue. The lumen can also be used inject contrast through a sidearm to confirm pericardial puncture, and to insert a wire into the pericardial space after puncture is confirmed. An optional second lumen 605 can be present which could allow for near simultaneous injection of contrast and advancement of the wire. The second lumen may contain a wire 601, which passes through the lumen 605, is positioned inside the outer needle 617. The lumen 605 allows for contrast injection and advancing the wire 601 into the tissue once access is attained. Optionally the pericardial needle 660 may include a second lumen containing a contrast needle. The contrast needle may be synchronized to release contrast with movement of the heart. An optional inner stylet 608 with a cautery tip or sharp cutting tip 607 is positioned inside the outer cautery needle 617. The stylet 608 has an optional handle 603 A controller 609 preferably also controls the functional activation of the cautery needle 617 as well as administration of cautery during use when penetrating a pericardia membrane.

The tip 607 of the stylet 608 may also independently puncture through tissue with or preferably without cautery. Preferably the cautery needle is mechanically advanced, with the stylet in the needle, until the tip is close to the pericardial membrane. The stylet is then removed and the blunt cautery needle tip is advanced further until it is in direct contact with the pericardial membrane.

The cautery needle 617 can provide rapid and brief cautery pulses when close to/in contact with the pericardial membrane. These pulses can be controlled by the controller 609. During contact of the cautery tip 606 with the pericardial membrane the controller 609 administers a cautery pulse to puncture or cut the pericardial membrane. For example, the puncture can be synchronized with systole.

To puncture the skin and advance through tissue, the cautery needle 617 may be advanced forward to allow penetration and advancement inside the tissue with or without the aid of the optional stylet 607. Once in close proximity to the pericardium (under fluoroscopy guidance), the pericardial needle 660 can be used for cauteral puncturing. An optional contrast syringe (not shown) may be connected through an inlet 602 of the lumen 605, or an optional second inlet of the lumen 605, with test injections done after or during each administration of cautery or puncture. Once the pericardium is punctured, contrast is seen filling the pericardial space. At this point, no additional punctures or cautery are done. A wire is optionally advanced into the pericardial space. The wire may be used as a guide for inserting a sheath into the pericardial space.

The controller is configured to administer a pulse of energy (high frequency alternating current) to the cautery needle. When the energy is electrical energy the controller may administer a single short pulse or a plurality of short pulses of electrical energy to the cautery needle. This energy exits at the needle tip which is positioned against the pericardial membrane, and thus penetrating it. The controller may be programmed such that administration of the electrical pulse is automatic and is triggered by detection of the heart phase or alternately may be administered manually through a human operator triggering the pulse by command to the controller.

The foregoing discussion discloses and describes merely exemplary embodiments. As will be understood by those skilled in the art, the present application may be embodied in other specific forms without departing from the spirit or essential characteristics thereof. Accordingly, the present disclosure is intended to be illustrative, but not limiting of the scope of the application, as well as other claims. The disclosure, including any readily discernible variants of the teachings herein, defines, in part, the scope of the foregoing claim terminology such that no inventive subject matter is dedicated to the public.

The invention claimed is:

1. A pericardial needle that punctures a pericardial membrane of a heart of a human patient, the pericardial needle comprising: an outer_cautery needle having a blunt cautery tip: an inner stylet having a sharp tip to puncture the pericardial membrane, the inner stylet being disposed inside the outer cautery needle; at least one of a first lumen having a wire passing through the first lumen and a second lumen having a contrast needle disposed inside the second lumen, wherein the at least one of the first lumen and the second lumen is affixed onto an inner surface of the outer cautery needle: and a controller that is configured to administer a cautery pulse to the blunt cautery tip through the outer cautery needle, wherein the controller is configured to track systole and diastole contraction phases of the heart for the administration of the cautery pulse through the outer cautery needle, and the pericardial needle is configured to advance toward the heart of the human patient to puncture, by cautery, the pericardial membrane of the heart in synchronization with a systole contraction phase of a mechanical activity of the heart of the human patient.

2. The pericardial needle according to claim 1, wherein the controller is configured to receive electrocardiogram signals from the human patient and detect the systole. the diastole, the mechanical activity of heart. and motion of the heart based on the electrocardiogram signals.

3. The pericardial needle according to claim 2, wherein the controller-is configured to monitor the electrocardiogram of the human patient and identify the phase of the mechanical activity of the heart of the human patient.

4. The pericardial needle according to claim 3, wherein the controller is configured to acquire the electrocardiogram of the human patient, detect a QRS complex within the electrocardiogram of the human patient, wait for a predetermined time after the controller detects QRS complex, and indicate a systole phase of the heart of the human patient when the predetermined time after the detected QRS complex has elapsed.

5. The pericardial needle according to claim 4, wherein the controller adjusts the predetermined time based on at least one of an age, a gender, a heart rate, a presence of an underlying heart disease, or a body mass index of the human patient.

6. The pericardial needle according to claim 5, wherein the controller is configured to detect the QRS complex within the electrocardiogram of the human patient based on a slope of the electrocardiogram of the human patient, and detect if the determined slope has exceeded a predetermined slope threshold.

7. The pericardial needle according to claim 6, wherein the controller is configured to adjust the predetermined slope threshold based on at least one of an age, a gender, a heart rate, a presence of an underlying heart disease, or a body mass index of the human patient.

8. The pericardial needle according to claim 7, wherein the controller is configured to detect[s] the QRS complex within the electrocardiogram of the human patient by determining a correlation between a time window of the electrocardiogram of the human patient and a predetermined QRS template, and determining if the determined correlation has exceeded a predetermined correlation threshold.

9. The pericardial needle according to claim 8, wherein the controller is configured to determine the predetermined QRS template based on a previously acquired QRS complex of the human patient.

10. The pericardial needle according to claim 9, wherein the controller is configured to detect the phase of the mechanical activity of the heart of the human patient by measuring a pressure at the tip of the needle, and determining if the measured pressure has fallen below a predetermined pressure threshold.

11. The pericardial needle according to claim 9, wherein the controller is configured to adjust a predetermined pressure threshold based on at least one of an age, a gender, a heart rate, a presence of an underlying heart disease, or a body mass index of the human patient.

12. The pericardial needle according to claim 1, wherein the first lumen has a first inlet outside the outer cautery needle to receive the wire and a second inlet outside the outer cautery needle to receive a second contrast syringe containing a test contrast agent: and the controller is further configured to administer the test contrast agent through the second contrast syringe and advance the wire through the pericardial membrane as soon as the pericardial membrane is punctured.

13. A pericardial needle that punctures a pericardial membrane of a heart of a human patient, the pericardial needle comprising: an outer cautery needle having a blunt cautery tip; an inner stylet having a sharp tip to puncture the pericardial membrane, the inner stylet being disposed inside the outer cautery needle; at least one of a first lumen having a wire passing through the first lumen and a second lumen having a contrast needle disposed inside the second lumen, wherein the at least one of the first lumen and the second lumen is affixed onto an inner surface of the outer cautery needle; a controller that is connected to the outer cautery needle and administers a cautery pulse to the outer cautery needle; wherein the controller is configured to track systole and diastole contraction phases of the heart to administer a cautery pulse through the inner cautery needle and advance the cautery needle through the pericardial membrane in synchronization with a detected systole contraction phase.

14. The pericardial needle according to claim 13, wherein the controller is configured to receive electrocardiogram signals from the human patient and detect the systole, the diastole, mechanical activity of heart, and motion of the heart based on the electrocardiogram signals.

15. The pericardial needle according to claim 14, wherein the controller is configured to monitor the electrocardiogram of the human patient and identifies a phase of the mechanical activity of the heart of the human patient.

16. The pericardial needle according to claim 15, wherein the controller is configured to acquire the electrocardiogram of the human patient, detect a QRS complex within the electrocardiogram of the human patient, wait for a predetermined time after the controller detects QRS complex, and indicate a systole phase of the heart of the human patient when the predetermined time after the detected QRS complex has elapsed.

17. The pericardial needle according to claim 16, wherein the controller is configured to adjust the predetermined time based on at least one of an age, a gender, a heart rate, a presence of an underlying heart disease, or a body mass index of the human patient.

18. The pericardial needle according to claim 17, wherein the controller is configured to detect the QRS complex within the electrocardiogram of the human patient based on a slope of the electrocardiogram of the human patient, and detect if the determined slope has exceeded a predetermined slope threshold.

19. The pericardial needle according to claim 18, wherein the controller is configured to adjust the predetermined slope threshold based on at least one of an age, a gender, a heart rate, a presence of an underlying heart disease, or a body mass index of the human patient.

20. The pericardial needle according to claim 13, wherein the first lumen has a first inlet outside the outer cautery needle to receive the wire and a second inlet outside the outer cautery needle to receive a second contrast syringe containing a test contrast agent, and the controller is further configured to administer the test contrast agent through the second contrast syringe and advance the wire through the pericardial membrane once as the pericardial membrane is punctured.

* * * * *